United States Patent
Park et al.

(10) Patent No.: US 12,233,257 B2
(45) Date of Patent: Feb. 25, 2025

(54) IMPLANTABLE LEAD WITH ADJUSTABLE ELECTRODE POSITION AND CONTROL SYSTEM THEREOF

(71) Applicant: SAMSUNG LIFE PUBLIC WELFARE FOUNDATION, Seoul (KR)

(72) Inventors: Eun Kyoung Park, Seoul (KR); Tae Kyung Kim, Seoul (KR); Tae Woo Kim, Seoul (KR); Min Hee Kang, Seoul (KR); Dong Il Choi, Seoul (KR); Kyu Sung Lee, Seoul (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 824 days.

(21) Appl. No.: 17/279,770

(22) PCT Filed: Jan. 6, 2021

(86) PCT No.: PCT/KR2021/000132
§ 371 (c)(1),
(2) Date: Mar. 25, 2021

(87) PCT Pub. No.: WO2021/157877
PCT Pub. Date: Aug. 12, 2021

(65) Prior Publication Data
US 2022/0016417 A1    Jan. 20, 2022

(30) Foreign Application Priority Data
Feb. 6, 2020    (KR) .................. 10-2020-0014418

(51) Int. Cl.
*A61N 1/05*    (2006.01)
*A61N 1/36*    (2006.01)

(52) U.S. Cl.
CPC ....... *A61N 1/0551* (2013.01); *A61N 1/36135* (2013.01)

(58) Field of Classification Search
CPC .................. A61N 1/0551; A61N 1/36135
See application file for complete search history.

(56) References Cited

U.S. PATENT DOCUMENTS

2007/0100406 A1 * 5/2007 Kollatschny ......... A61N 1/0551
607/116
2008/0046049 A1    2/2008 Skubitz et al.
(Continued)

FOREIGN PATENT DOCUMENTS

CN    109513111 A * 3/2019 ........... A61N 1/0563
EP    2389975 A1 * 11/2011 ........... A61N 1/0551
(Continued)

OTHER PUBLICATIONS

International Search Report from WIPO in Application No. PCT/KR2021/000132 dated Jun. 9, 2021, 3 pages.

*Primary Examiner* — James M Kish
*Assistant Examiner* — Laura Hodge
(74) *Attorney, Agent, or Firm* — Dilworth IP, LLC

(57) ABSTRACT

An implantable lead having adjustable electrode locations and a system for controlling the same. The implantable lead may include a plurality of first electrodes exposed and formed at an upper part of a main body at given intervals, a plurality of second electrodes coupled to a stepped lower part of the main body and configured to deliver a stimulus signal to a core area into which the lead is inserted, and a plurality of signal lines embedded in the main body and configured to connect the first electrodes and the second electrodes in a one-to-one manner. In this case, a slot for coupling and up and down movement of the second electrodes may be formed in the lower part. As the second electrodes are individually moved along the slot by an (Continued)

external force acting on the signal lines, locations of the second electrodes in the lower part may be adjusted.

11 Claims, 7 Drawing Sheets

(56) References Cited

U.S. PATENT DOCUMENTS

| | | | | |
|---|---|---|---|---|
| 2010/0145221 A1* | 6/2010 | Brunnett | ............. | A61N 1/0556 |
| | | | | 607/116 |
| 2011/0264180 A1* | 10/2011 | Hamilton | ............. | A61N 1/0558 |
| | | | | 607/117 |
| 2012/0071936 A1* | 3/2012 | Pianca | ................ | A61N 1/0553 |
| | | | | 607/2 |
| 2014/0039587 A1 | 2/2014 | Romero | | |
| 2015/0360023 A1* | 12/2015 | Howard | ............... | A61N 1/0534 |
| | | | | 607/116 |
| 2016/0038733 A1* | 2/2016 | Robinson | ................. | A61N 1/18 |
| | | | | 607/116 |
| 2016/0317053 A1* | 11/2016 | Srivastava | ......... | A61B 18/1492 |

FOREIGN PATENT DOCUMENTS

| | | | | |
|---|---|---|---|---|
| EP | 3603721 A1 | 2/2020 | | |
| JP | 2017-517374 A | 6/2017 | | |
| JP | 6490839 A | 3/2019 | | |
| KR | 10-1701757 B1 | 2/2017 | | |
| WO | WO-2019211314 A1 * | 11/2019 | ............. | A61B 5/002 |

* cited by examiner

IMPLANTABLE LEAD WITH ADJUSTABLE ELECTRODE POSITION AND CONTROL SYSTEM THEREOF

BACKGROUND

1. Technical Field

The present disclosure relates to an implantable lead having adjustable electrode locations and a system for controlling the same, and more particularly, to a structure of an implantable lead which can simplify corrective surgery after surgery and can maximize a stimulus effect because the location of an electrode can be randomly adjusted, and a system and method for controlling the same.

2. Related Art

Neuromodulation is a treatment method of adjusting a function of the body by stimulating a neurocircuit through an electric stimulus for a specific portion of a brain or a nerve, and is used to ameliorate a Parkinson's disease, chronic pain, dystonia, etc.

Neuromodulation utilizes an insertion type medical device in order to deliver an accurate electric pulse. A nerve stimulator basically consists of an implantable pulse generator, an extension, and a lead. The implantable pulse generator is implanted into the body and the lead is placed near a specific nerve, enabling a fine electric stimulus for a local area.

It is important to check the location of an electrode after surgery because a clinical course for each patient may be different depending on the location of the electrode. After the implant surgery of the nerve stimulator and the lead, a location or form of the lead may be changed or changed due to a physical collision or inside or outside pressure. If a sufficient fine electric stimulus is not provided to a nerve due to the deformation in or escape of the lead, surgery for re-correcting the location of the lead needs to be performed.

However, the operation of re-correcting the location of the lead is difficult surgery that needs the skin incision and may damage a surrounding muscle, bone or blood vessel, and thus is not an easy problem in terms of the quality of life of a patient or the stability of surgery and a medical device.

PRIOR ART DOCUMENT

Patent Document

1. Japanese Patent No. 6490839 (Mar. 8, 2019)

SUMMARY

Various embodiments are directed to providing a lead whose area to which a fine electric stimulus will be delivered is adjustable by controlling the location of an electrode itself through external control without complicated re-surgery although the location of the lead itself is changed due to a physical collision or a change in inside or outside pressure.

Also, various embodiments are directed to providing a control system configured to enable external control over the lead to be accurately performed and to easily monitor a nerve signal for a core area into which the lead is inserted.

In an embodiment, an implantable lead having adjustable electrode locations may include a plurality of first electrodes exposed and formed at an upper part of a main body at given intervals, a plurality of second electrodes coupled to a stepped lower part of the main body and configured to deliver a stimulus signal to a core area into which the lead is inserted, and a plurality of signal lines embedded in the main body and configured to connect the first electrodes and the second electrodes in a one-to-one manner. In this case, a slot for coupling and up and down movement of the second electrodes may be formed in the lower part. As the second electrodes are individually moved along the slot by an external force acting on the signal lines, locations of the second electrodes in the lower part may be adjusted.

In an embodiment, each of the second electrodes may include an exposed part configured to surround the outside of the lower part and having a ring shape, and a connection part elongated toward the center of the exposed part, led in the slot, and connected to each of the signal lines.

In an embodiment, the connection parts of the second electrodes may have different lengths in order to prevent a collision between the signal lines.

In an embodiment, each of the second electrodes may further include insulating members provided at the top and bottom surfaces of the exposed part in order to prevent the occurrence of a short circuit attributable to a contact between the second electrodes.

In an embodiment, the implantable lead may further include a fastening member coupled to the upper part of the main body and configured to fix movements of the signal lines.

In an embodiment, a system for controlling an implantable lead having adjustable electrode locations may include the implantable lead according to the aforementioned embodiment, a forceps electrically connected to the first electrodes, a signal line driving module connected to the signal lines and configured to individually control movements of the signal lines, and a processor configured to receive a nerve signal from the lead, digitize the nerve signal, and control an operation of the signal line driving module.

In an embodiment, the forceps may include a handle in which a wire for delivering the stimulus signal to the lead is led and disposed and a fixing part coupled to the upper part of the main body and configured to connect the lead and the forceps.

In an embodiment, the fixing part may include the wire extended from the handle and a plurality of electrode contacts connected to the wire.

In an embodiment, the forceps may further include a guider provided at the top of the fixing part on one side thereof and configured to seat the lead at a home position of the fixing part so that the first electrodes and the electrode contacts are brought into contact with each other.

In an embodiment, the signal line driving module may include a motor configured to provide a driving force for adjusting movements of the signal lines in response to a control signal from the processor, and a grabber connected to the signal lines.

DETAILED DESCRIPTION

Figure 1:
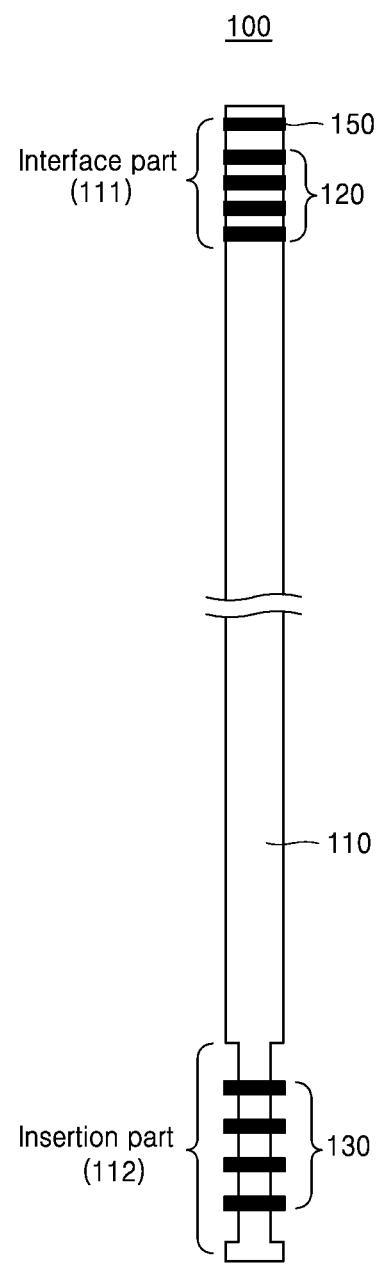
FIG. 1 is a front view illustrating an implantable lead according to an embodiment of the present disclosure.

Hereinafter, terms used in this specification are briefly described, and the present disclosure is described in detail.

Terms used in the present disclosure are common terms currently and widely used by taking into consideration functions in the present disclosure, but the terms may be changed depending on an intention of a technician skilled in the art, a precedent, or the advent of a new technology. Furthermore, in a specific case, some terms are randomly selected by the applicant. In this case, the meaning of a corresponding term will be described in detail in the corresponding description of the invention. Accordingly, terms used in the present disclosure should be defined based on their substantial meanings and contents over the present disclosure, not the simple names of the terms.

Throughout the specification, unless explicitly described to the contrary, the word "include" will be understood to imply the further inclusion of stated elements, not the exclusion of any other elements. Furthermore, the term " . . . part", "module" or "unit" described in the specification means a unit for processing at least one function or operation, and the unit may be implemented by hardware or software or a combination of hardware and software. Furthermore, throughout the specification, when it is described that one part is "connected" to another part, the one part may be "directly connected" to the another part or may be "indirectly connected" to the another part "with a still another part interposed therebetween."

Embodiments of the present disclosure are described hereinafter in detail with reference to the accompanying drawings, in order for a person having ordinary skill in the art to which the present disclosure pertains to easily carry out the present disclosure. The present disclosure may be implemented in various different ways, and is not limited to the disclosed embodiments herein. In the drawings, in order to clearly describe the present disclosure, parts unrelated to the description are omitted, and similar reference numbers are used to refer to similar parts throughout the specification.

Hereinafter, the present disclosure is described in detail with reference to the accompanying drawings.

FIG. 1 is a front view illustrating an implantable lead 100 according to an embodiment of the present disclosure.

Referring to FIG. 1, the implantable lead 100 according to an embodiment of the present disclosure may be divided into an interface part 111 to which a control system to be described later is connected and an insertion part 112 inserted into a target location. A plurality of first electrodes 120 electrically connected to the control system in order to receive a stimulus signal from the control system may be spaced and formed in the interface part 111, that is, the upper part of a main body 110 of the lead. The plurality of first electrodes may be integrated with the main body 110 so that external surfaces of the first electrodes are exposed for a connection with the control system.

The insertion part 112 is the stepped lower part of the main body 110. A plurality of second electrodes 130 for receiving a stimulus signal from the interface part 111 and generating an electric stimulus may be disposed in one part of the insertion part, which has a narrower diameter than the main body 110. In this case, the plurality of first electrodes 120 may be connected to the plurality of second electrodes 130 in a one-to-one manner through signal lines 140 disposed within the main body 110. Accordingly, the number of first electrodes 120 and the number of second electrodes 130 may be the same.

Referring to FIG. 1, a fastening member 150 for fixing movements of the signal lines 140 and the second electrodes 130 may be formed in the interface part 111 of the main body 110. The signal lines 140 are used to connect the first electrodes 120 and the second electrodes 130 and also used as control means for adjusting the locations of the second electrodes 130. The signal lines 140 need to move only in a control process for adjusting and changing the locations of the second electrodes 130. Accordingly, the fastening member using a screw fastening method may be connected to the upper part of the main body 110 so that the signal lines 140 are not moved in the state in which the adjustment of locations of the second electrodes 130 is completed.

The main body 110 of the implantable lead 100 according to an embodiment of the present disclosure may be made of a flexible material in order for a shape thereof to be easily changed. That is, the main body 110 may be fabricated using a material that is flexible and has high durability. The main body 110 is inserted into the human body and thus may be fabricated using a material harmless to the human body for a long period. For example, the main body 110 may be fabricated using polyurethane or the like.

Furthermore, a hollow may be formed in the innermost space of the main body 110. A support may be led and disposed in the hollow. The support corresponding to the center axis of the lead 100 generally supports the structure of the lead 100 in order to prevent the main body 110 from being bent or a shape of the main body 110 from being changed while the lead 100 is inserted into a target location. Accordingly, after the lead 100 is inserted, the support may be removed by a clinician who performs neurostimulation.

Figure 2A:
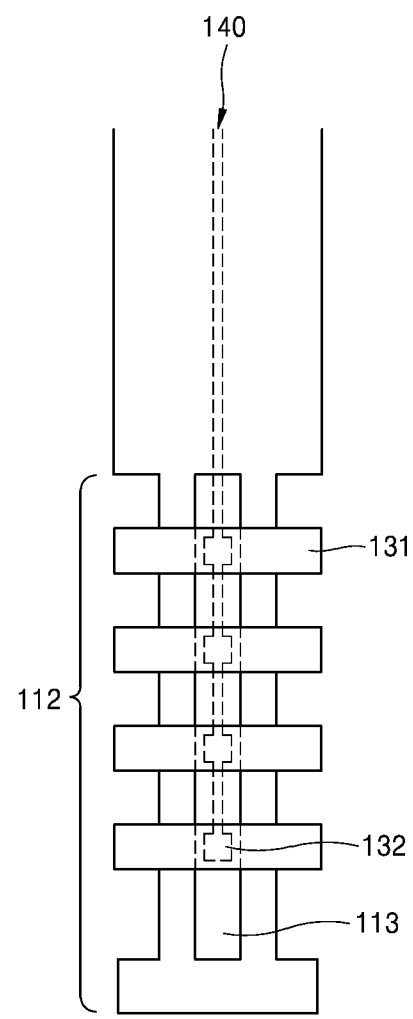
FIG. 2A is a front perspective view of an insertion part of the implantable lead according to an embodiment of the present disclosure.
Figure 2B:
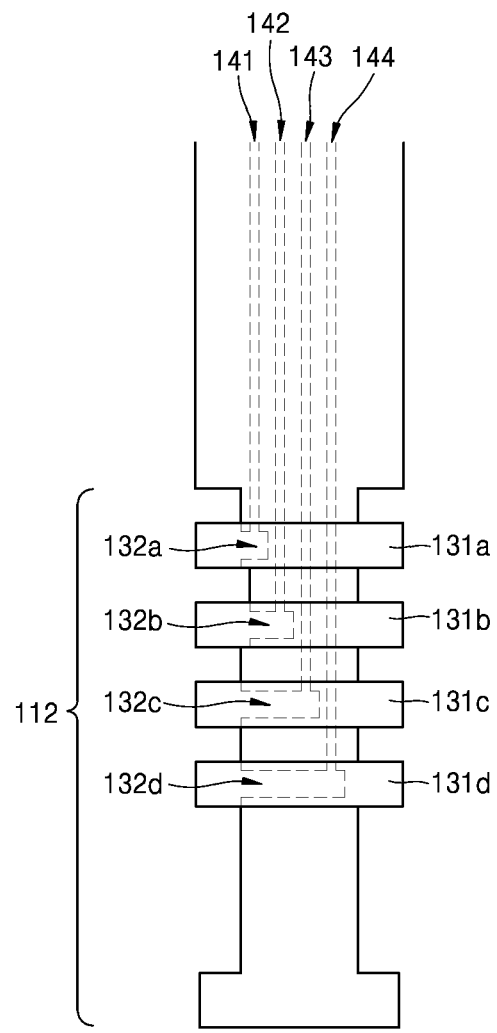
FIG. 2B is a side perspective view illustrating the insertion part of the implantable lead according to an embodiment of the present disclosure.

FIG. 2A is a front perspective view of the insertion part 112 of the implantable lead 100. FIG. 2B is a side perspective view illustrating the insertion part 112 of the implantable lead 100.

Referring to FIG. 2A, a slot 113 for enabling the second electrodes 130 to be coupled to the insertion part 112 and also to move within the insertion part 112 up and down may be formed in the insertion part 112 according to an embodiment of the present disclosure. That is, the slot 113 corresponds to a coupling element into which connection parts 132 of the second electrodes 130 are inserted and also a guide element that enables the second electrodes 130 to move up and down. Accordingly, each of the second electrodes 130 individually controlled by the signal lines 140 may move up and down along the slot 113, so that a portion to which an electric stimulus is delivered may be adjusted.

Referring to FIG. 2B, the connection parts 132 of the respective second electrodes 130 according to an embodiment of the present disclosure may be formed to have different lengths, and may be individually connected to the signal lines 140, respectively. The reason why the connection parts 132 are formed to have different lengths is to prevent a collision and a short circuit between the signal lines 140. For example, if the insertion part 112 is equipped with four second electrodes 130, the lengths of connection parts 132a, 132b, 132c, and 132d may be gradually increased in order of an upper second electrode, an upper middle second electrode, a lower middle second electrode, and a lower second electrode. In this case, since four signal lines 141, 142, 143, and 144 are connected to the connection parts 132a, 132b, 132c, and 132d of the second electrodes 130, respectively, the four signal lines 141, 142, 143, and 144 may be disposed within the main body 110 while maintaining given intervals therebetween depending on the lengths of the connection parts 132a, 132b, 132c, and 132d. Through such a structure, although the four signal lines 141, 142, 143, and 144 are individually controlled up and down, the second electrodes 130 can be stably moved without a collision or a short circuit therebetween.

Figure 3A:
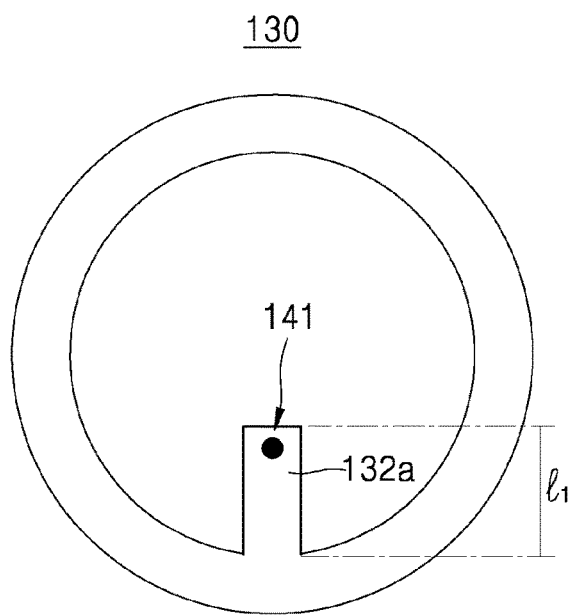
FIGS. 3A and 3B are plan views illustrating a second electrode according to an embodiment of the present disclosure.
Figure 3B:
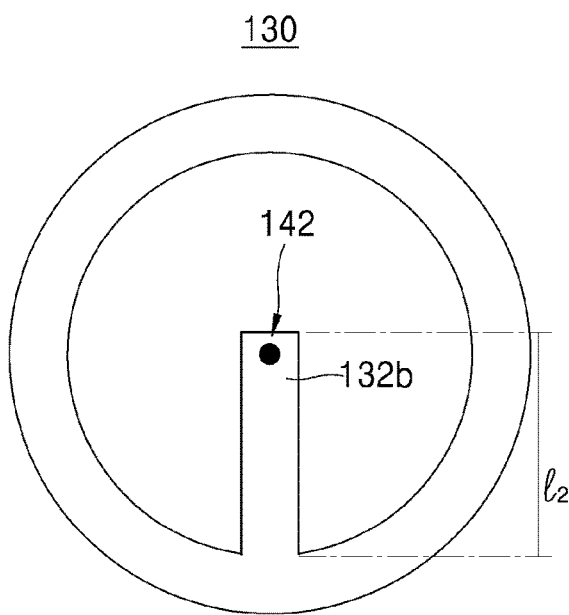

FIGS. 3A and 3B are plan views illustrating the second electrode according to an embodiment of the present disclosure.

Referring to FIGS. 3A and 3B, each of the second electrodes 130 according to an embodiment of the present disclosure may include an exposed part 131 configured to surround the outside of the lower part and having a ring shape, and the connection part 132 elongated toward the center of the exposed part 131, led in the slot 113 and connected to each of the signal lines 140. In this case, the outside diameter of the exposed part 131 may be the same as the diameter of the main body 110 in order to prevent the lead 100 from being caught in a process of inserting the lead 100. Since the diameter of the main body 110 is constant, all the second electrodes 130 may be formed to have the same outside diameter. In contrast, as described above, the connection parts 132 may be formed to have different lengths in order to secure a space for preventing a collision and a short circuit between the signal lines 140. For example, if the length of the connection part 132 of a second electrode, such as FIG. 3A, is $I_1$, the length of the connection part 132 of a second electrode, such as FIG. 3B, disposed under the second electrode, such as FIG. 3A, may be $I_2$ greater than $I_1$.

Although not illustrated, each of the second electrodes 130 according to an embodiment of the present disclosure may further include insulating members provided at the top and bottom surfaces of the exposed part 131 in order to prevent the occurrence of a short circuit attributable to a contact between the second electrodes 130. Each of the second electrodes 130 is made of metal that generates an electric stimulus. Accordingly, there is a danger that a short circuit may occur due to a mutual contact between the second electrodes 130 adjacent to each other up and down in an arrangement, such as FIG. 2. In order to prevent the occurrence of a short circuit attributable to a contact, the insulating members may be provided at the top and bottom of each of the plurality of second electrodes 130 except the side of the second electrode.

Figure 4:
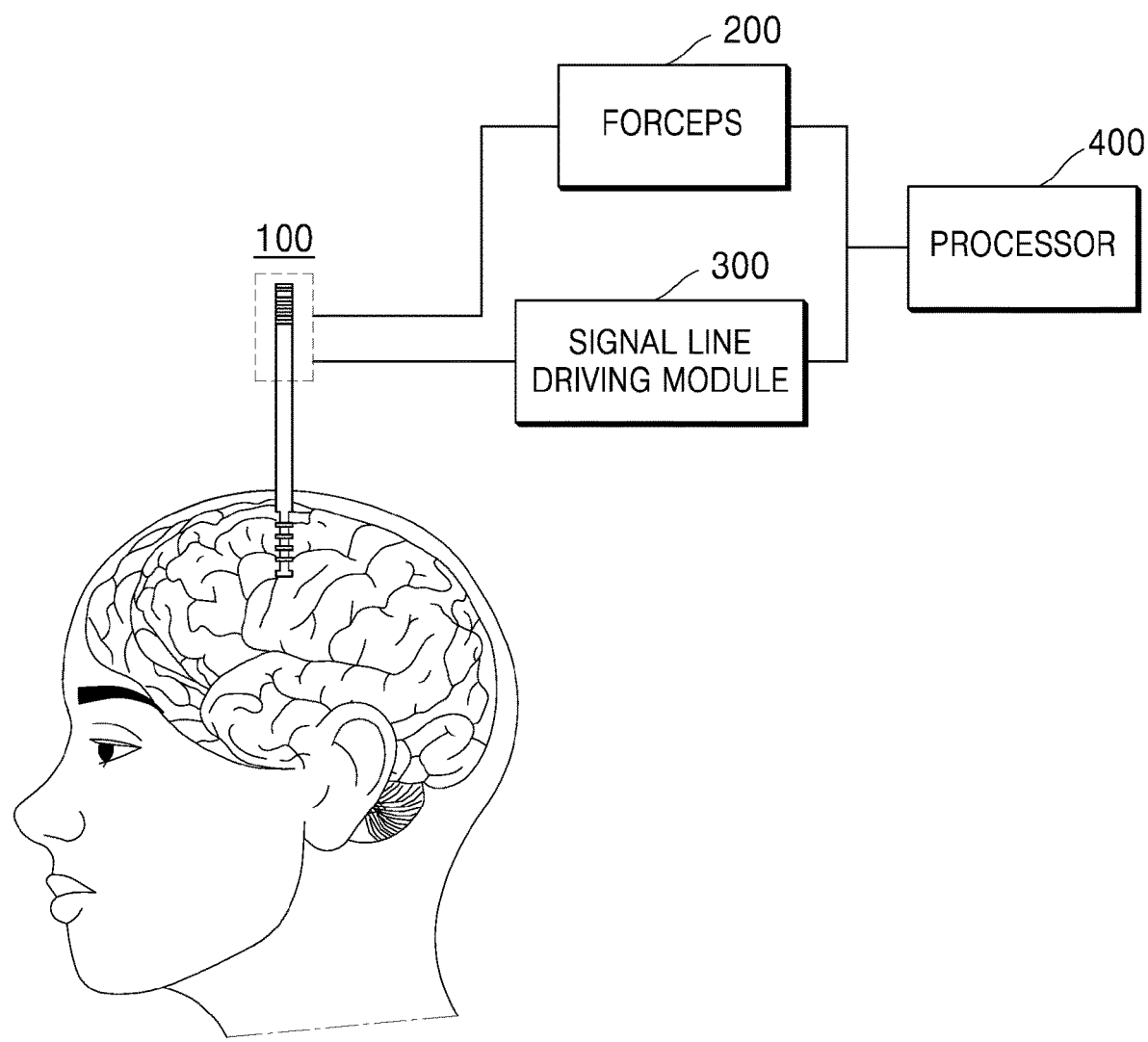
FIG. 4 is a conceptual diagram illustrating a system for controlling the implantable lead according to an embodiment of the present disclosure.

FIG. 4 is a conceptual diagram illustrating a system for controlling the implantable lead 100 according to an embodiment of the present disclosure.

Referring to FIG. 4, the system for controlling the implantable lead 100 according to an embodiment of the present disclosure may include the implantable lead 100 according to the aforementioned embodiment, which is inserted into a target location, a forceps 200 electrically connected to the first electrodes 120, a signal line driving module 300 connected to the signal lines 140 and configured to individually control movements of the signal lines 140, and a processor 400 configured to receive a nerve signal from the lead 100, digitize the nerve signal, and control an operation of the signal line driving module 300.

For example, the interface part 111 of the lead 100 and the forceps 200 may be electrically connected so that the processor 400 and the lead 100 mutually transmit and receive signals. Furthermore, in order to control the signal lines 140 for adjusting the locations of second electrodes 130 of the lead 100, the interface part 111 of the lead 100 and the signal line driving module 300 may be mechanically connected.

The processor 400 may transmit a stimulus signal to the lead 100 through the forceps 200. Furthermore, the processor 400 may receive, through the forceps 200, a nerve signal measured by the lead 100. The processor 400 may digitize the nerve signal measured by the lead 100, and may output the digitized signal to a separate external device (e.g., a smartphone, a PC, a table PC or a laptop) through wired or wireless network communication. The processor 400 may generate a control signal based on the nerve signal received from the lead 100, and may control an operation of the signal line driving module 300.

Figure 5:
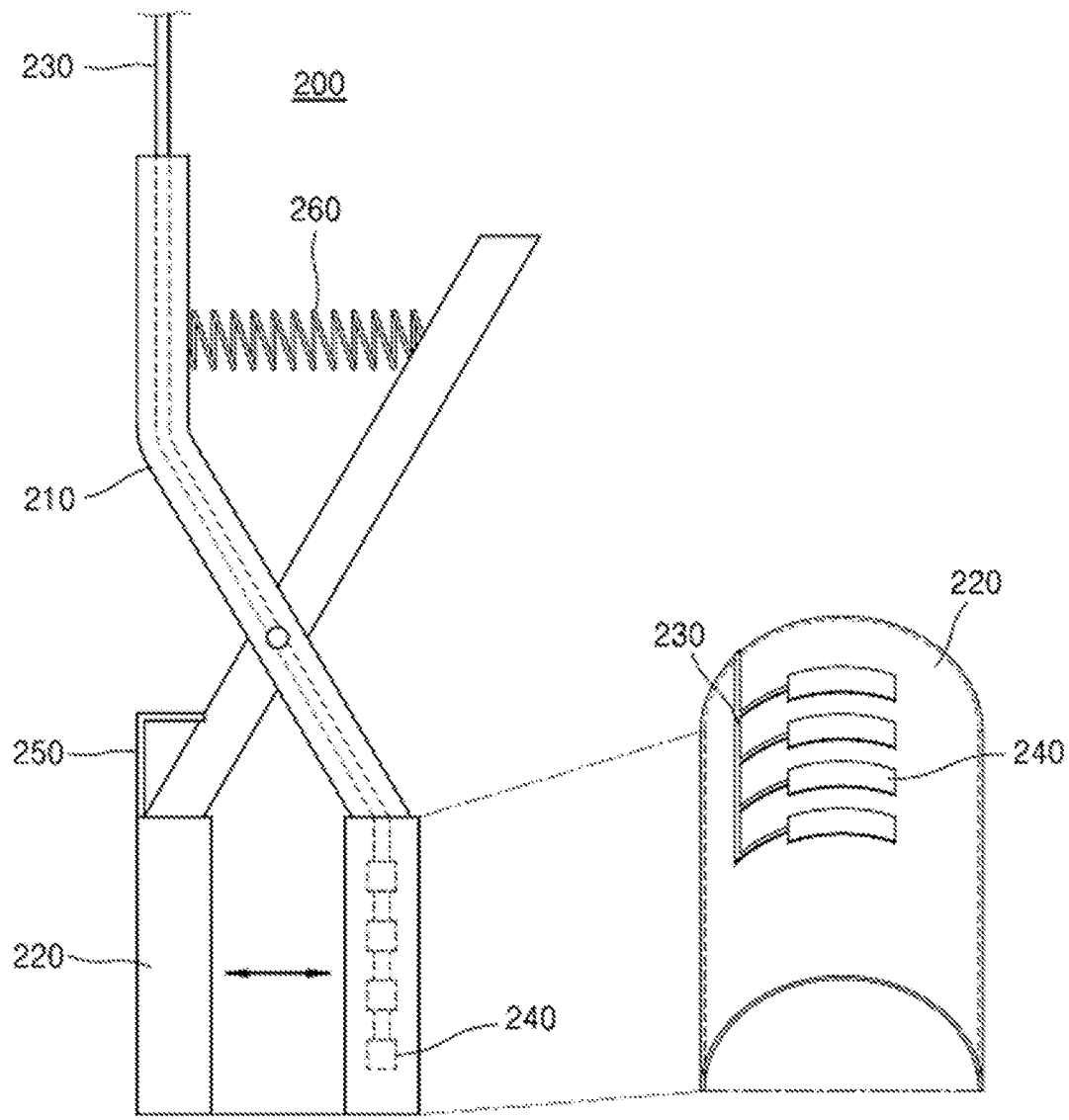
FIG. 5 is a conceptual diagram illustrating a forceps according to an embodiment of the present disclosure.

FIG. 5 is a conceptual diagram illustrating the forceps 200 according to an embodiment of the present disclosure.

Referring to FIG. 5, the forceps 200 according to an embodiment of the present disclosure may include a handle 210 in which a wire 230 for delivering a stimulus signal to the lead 100 is lead and disposed, and a fixing part 220 coupled to the upper part of the main body 110 and configured to connect the lead 100 and the forceps 200. For example, the wire 230, that is, a passage for the transmission and reception of a stimulus signal or a nerve signal, may be led in one arm of the cliptype handle 210 and extended up to the fixing part 220. In this case, for a connection with the processor 400, the signal lines 140 may be exposed and extended to the top of the handle 210 to which the fixing part 220 is not coupled.

The fixing part 220 configured to surround the upper part of the lead 100 may be provided at the bottom of the handle 210. The fixing part 220 may consist of two fixing units, each having a semicylinder shape, so that the fixing part can be in close contact with the lead 100. In this case, one of the two fixing units, each having a semicylinder shape, may include the wire 230 extended within one arm of the handle 210 on one side thereof and a plurality of electrode contacts 240 connected to the wire 230. That is, for a connection between the processor 400 and the first electrodes 120 provided in the interface part 111 of the lead 100, the electrode contacts 240 corresponding to the number and locations of the first electrodes 120 may be provided on the inner wall of the fixing unit having a semicylinder shape.

The forceps 200 according to an embodiment of the present disclosure may further include a guider 250 provided at the top of the fixing part 220 on one side thereof and configured to seat the lead 100 at the home position of the fixing part 220 so that the first electrodes 120 and the electrode contacts 240 are brought into contact with each other. For example, the guider 250 may be provided at the top of a fixing unit that belongs to the two fixing units, each having a semicylinder shape, and that is not equipped with the electrode contacts 240. The guider 250 may be fabricated to have a ]-shaped section. That is, the guider 250 functions to enable the first electrodes 120 of the interface part 111 of the lead 100 and the electrode contacts 240 of the forceps 200 to be accurately matched with each other and to prevent the lead 100 from escaping toward an opened upper part of the fixing part 220.

Furthermore, the forceps 200 according to an embodiment of the present disclosure may further include an elastic member 260 provided between both the arms of the handle 210. The elastic member 260 is an element for providing manipulation convenience to a clinician who uses the forceps 200 and also providing a coupling force to the fixing part 220. That is, the elastic member 260 provides the coupling force so that the two fixing units can maintain the state in which the two fixing units are brought into contact with each other, unless a separate external force acts on both the arms of the handle 210. Accordingly, the state in which the lead 100 is stably coupled to the fixing part 220 can be maintained through the elastic member 260.

Figure 6:
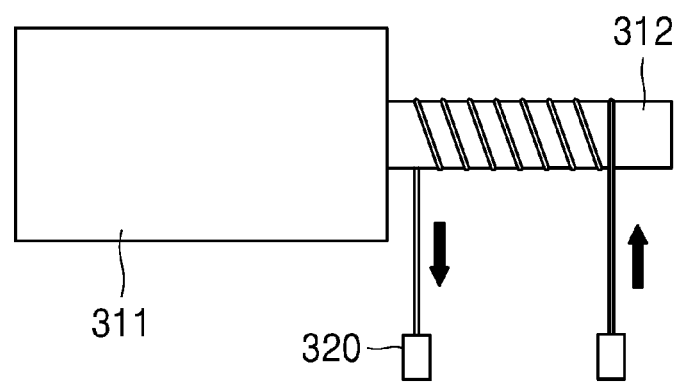
FIG. 6 is a conceptual diagram illustrating a signal line driving module according to an embodiment of the present disclosure.

FIG. 6 is a conceptual diagram illustrating the signal line driving module 300 according to an embodiment of the present disclosure.

The signal line driving module 300 according to an embodiment of the present disclosure may include a motor configured to provide a driving force for adjusting movements of the signal lines 140 in response to a control signal from the processor 400 and a grabber 320 connected to the signal lines 140. The motor may include a motor main body 311 configured to receive the control signal from the processor 400 and generate a driving force in response thereto and a motor rotation shaft 312 rotated by the driving force generated by the motor main body 311. In this case, the grabber 320 may be attached to both ends of the signal lines 140 wound on the motor rotation shaft 312. One grabber 320 may be connected to one motor rotation shaft 312 through a signal line. For example, if four signal lines 140 are included in the lead 100, the signal line driving module 300 may include four motor rotation shafts 312 and four grabbers 320.

The adjustment of locations of the second electrodes 130 of the lead 100 using the system for controlling the implantable lead may be performed through the following process.

When power is applied to the system for controlling the implantable lead, the processor 400 may perform initialization processes, such as location zero adjustment for the motor and a communication connection with an external device for control. When the lead 100 is inserted into a target location in the state in which the support is not removed by a clinician, the signal lines 140 and the grabber 320 of the signal line driving module 300 may be connected.

When the connection between the signal line driving module 300 and the lead 100 is completed, the forceps 200 and the lead 100 may be connected so that the electrodes 111b of the interface part 111 of the lead 100 come into contact with correct locations of the electrode contacts 240 in the state in which the upper part of the lead 100 is brought into contact with the guider 250 of the forceps 200. When the connection between the forceps 200 and the lead 100 is completed, a nerve signal obtained by the lead 100 may be transmitted to the processor 400 in real time.

When the processor 400 generates a control signal based on the nerve signal and transmits the control signal to the signal line driving module 300, the signal line driving module 300 may drive the motor up to the target location to which an electric stimulus of the second electrodes 130 will be delivered. If each of the second electrodes 130 reaches the target location or a stop signal is received from the processor 400 while the motor is driven, the signal line driving module 300 may stop the driving of the motor.

When the final locations of the second electrodes 130 are determined through the repeated driving and stop process of the motor based on the control signal, the connection between the processor 400 and the forceps 200 and the signal line driving module 300 may be released. When the insertion of the lead 100 is completed, the forceps 200 and the support may be sequentially removed from the lead 100. Furthermore, the signal lines are fully fixed through screw fastening to the fastening member 150. After the signal lines are fully fixed, all the grabbers 320 of the signal line driving module 300 may be removed.

According to an embodiment of the present disclosure, the signal processing process by the processor 400 in the aforementioned method may be written in the form of a computer-executable program, and may be implemented in a general-purpose digital computer that drives the program using a computer-readable medium. Furthermore, a structure of data used in the signal processing process by the processor 400 may be recorded on a computer-readable medium through several means. A recording medium on which an executable computer program or code for performing such a process is recorded should not be understood to include transitory targets, such as carrier waves or signals.

According to the implantable lead and the system for controlling the same, which are provided as embodiments of the present disclosure, the following significant effects may be achieved.

1. A correction can be performed without a re-surgery by using the present disclosure if a location correction for an electric stimulus portion is necessary after neuromodulation is performed in a conventional technology.
2. A movement or escape of an electrode can be conveniently adjusted through an external controller.
3. Positive effects can be provided to the quality of life of a patient and the stability and lifespan of a medical device because surgery for correcting an electrode becomes unnecessary.
4. A stimulus effect on a target nerve can be maximized by a simple correction process for an electrode.

The description of the present disclosure is illustrative, and a person having ordinary knowledge in the art to which the present disclosure pertains will understand that the present disclosure may be easily modified in other detailed forms without changing the technical spirit or essential characteristic of the present disclosure. Accordingly, it should be construed that the aforementioned embodiments are only illustrative in all aspects, and are not limitative. For example, elements described in the singular form may be carried out in a distributed form. Likewise, elements described in a distributed form may also be carried out in a combined form.

The scope of the present disclosure is defined by the appended claims rather than by the detailed description, and all changes or modifications derived from the meanings and scope of the claims and equivalents thereto should be interpreted as being included in the scope of the present disclosure.

What is claimed is:

1. An implantable lead having adjustable electrode locations, comprising:
    a main body having an upper part and a stepped lower part, the lower part having a narrower diameter than the upper part;
    a plurality of first electrodes exposed and formed in the upper part of the main body at given intervals;
    a plurality of second electrodes coupled to, and configured to move up and down with respect to, the stepped lower part of the main body and configured to deliver a stimulus signal to a core area into which the lead is inserted; and
    a plurality of signal lines embedded in the main body and configured to connect the first electrodes and the second electrodes in a one-to-one manner, wherein the lower part includes a slot for coupling with the second electrodes and enabling the second electrodes to move up and down, and wherein the plurality of second electrodes are individually movable along the slot by an external force acting on the signal lines, thereby adjusting the locations of the second electrodes in the lower part.

2. The implantable lead of claim 1, wherein each of the second electrodes comprises:

an exposed part configured to surround an outside of the lower part and having a ring shape, and a connection part elongated inward from the exposed part toward a center of the exposed part, extending in the slot, and connected to a respective one of the signal lines in the main body.

3. The implantable lead of claim 2, wherein the connection parts of each of the second electrodes have different lengths in order to prevent a collision between the signal lines.

4. The implantable lead of claim 2, wherein each of the second electrodes further comprises insulating members provided at top and bottom surfaces of the exposed part in order to prevent occurrence of a short circuit attributable to a contact between the second electrodes.

5. The implantable lead of claim 2, wherein the exposed part has a same diameter as the upper part of the main body.

6. The implantable lead of claim 1, further comprising a fastening member coupled to the upper part of the main body and configured to fix movements of the signal lines.

7. A system for controlling an implantable lead having adjustable electrode locations, comprising:

the implantable lead according to claim 1;

a forceps electrically connected to the first electrodes;

a signal line driving module including a motor and a grabber to individually control movements of the signal lines; and a processor configured to receive a nerve signal from the lead, digitize the nerve signal, and control an operation of the signal line driving module.

8. The system of claim 7, wherein the forceps comprises:

a handle in which a wire for delivering the stimulus signal to the lead is led and disposed, and a fixing part coupled to the upper part of the main body and configured to connect the lead and the forceps.

9. The system of claim 8, wherein the fixing part comprises:

the wire extended from the handle, and a plurality of electrode contacts connected to the wire.

10. The system of claim 9, wherein the forceps further comprises a guider provided at a top of the fixing part on one side thereof and configured to seat the lead at a home position of the fixing part so that the first electrodes and the electrode contacts are brought into contact with each other.

11. The system of claim 7, wherein the signal line driving module further comprises a grabber connected to the signal lines, wherein the motor configured to provide a driving force for adjusting movements of the signal lines in response to a control signal from the processor.

* * * * *